United States Patent [19]

Morawa et al.

[11] Patent Number: 5,788,700
[45] Date of Patent: Aug. 4, 1998

[54] APPARATUS AND METHOD FOR THE ALIGNMENT OF A TOTAL KNEE PROSTHESIS

[75] Inventors: Lawrence G. Morawa, Dearborn, Mich.; Kenneth H. Trimmer, Waldwick, N.J.

[73] Assignee: Osteonics Corp., Allendale, N.J.

[21] Appl. No.: 741,434

[22] Filed: Oct. 30, 1996

[51] Int. Cl.[6] ............................................. A61B 17/56
[52] U.S. Cl. .................................................. 606/88
[58] Field of Search ......................... 606/86, 87, 88, 606/89, 96

[56] References Cited

U.S. PATENT DOCUMENTS

| | | |
|---|---|---|
| 3,596,554 | 8/1971 | Low. |
| 4,653,488 | 3/1987 | Kenna et al. ................... 606/88 |
| 4,938,762 | 7/1990 | Wehrli ........................... 606/88 |
| 5,282,803 | 2/1994 | Lackey ........................... 606/80 |
| 5,462,550 | 10/1995 | Dietz et al. .................... 606/86 |

OTHER PUBLICATIONS

Duracon® The Tibial System, Howmedica, pp. 12–15, 1994.

*Primary Examiner*—Michael Buiz
*Assistant Examiner*—David O. Reip
*Attorney, Agent, or Firm*—Arthur Jacob

[57] ABSTRACT

A tibial resection guide is aligned with the direction of the mechanical axis of the leg of a recipient of a total knee prosthesis through the use of a proximal alignment member at the proximal portion of an external tibial alignment shaft coupled to the tibia, the proximal alignment member having a guideway for the reception of an external alignment rod affixed to the distal femur of the recipient and so as to extend in the direction of the mechanical axis.

16 Claims, 4 Drawing Sheets

APPARATUS AND METHOD FOR THE ALIGNMENT OF A TOTAL KNEE PROSTHESIS

The present invention relates generally to apparatus and method for establishing the correct alignment and orientation for a knee prosthesis during total knee arthroplasty surgery and pertains, more specifically, to determining the correct position and orientation of cutting guides with respect to the mechanical axis of a patient's femur so that the femur and the tibia can be cut to fit the knee prosthesis and the knee prosthesis will be implanted in an anatomically correct orientation. In particular, the present invention is directed to attaining appropriate alignment of a tibial resection guide relative to the mechanical axis of the femur and, consequently, relative to the mechanical axis of the leg of the recipient of the knee prosthesis.

During knee resurfacing arthroplasty, commonly called knee replacement surgery, the distal surfaces of the femur are cut away and replaced with a metal component to simulate the bearing surfaces of the femur. The proximal surface of the tibia is modified in a similar way, to provide a metal-backed plastic bearing surface. The metal femoral component of the new prosthetic joint transfers the weight of the patient to the tibial component such that the joint can support the patient's weight and provide a near-normal motion of the knee joint.

Several studies have indicated that the long term performance of a prosthetic knee joint is dependant on how accurately the components of the knee joint are implanted with respect to the weight bearing axis of the patient's leg. In a correctly functioning knee, the weight bearing axis passes through the center of the head of the femur, the center of the knee and the center of the ankle joint. This weight bearing axis typically is located by analyzing an X-ray image of the patient's leg, taken while the patient is standing.

The X-ray image is used to locate the center of the head of the femur and to calculate the position of the head relative to selected landmarks on the femur. The selected landmarks are then found on the patient's femur during surgery and the calculations used to estimate the actual position of the femoral head. These two pieces of information are used to determine the correct alignment of the weight bearing axis for the femur, commonly referred to as the mechanical axis of the femur. To completely define the correct position for the femoral component of the knee prosthesis, the correct relationship between the center of the femoral head and the knee joint and the rotation of the knee joint about the mechanical axis must be established. This information is determined from landmarks on the distal portion of the femur. The correct alignment for the tibial component of the knee prosthesis ordinarily is determined by finding the center of the ankle joint and relating its position to landmarks on the tibia. This point and the center of the proximal tibial plateau are used to define the weight bearing axis, or mechanical axis, of the tibia. The correct relationship between the ankle joint and the knee joint and the rotation of the knee joint about the mechanical axis are determined by reference to the distal portion of the femur and landmarks on the tibial plateau.

Various mechanical alignment instruments are used to assist the surgeon in making cuts on the distal femur and proximal tibia which will allow the femoral and tibial components of the prosthetic knee implant to be attached to the femur and tibia. These mechanical alignment instruments permit the surgeon to fix cutting guides in place with respect to the selected landmarks on the bones so that the cuts will be correctly oriented with respect to the mechanical axes determined from the X-ray image.

There are two general types of alignment instruments in common use. These are intramedullary and extramedullary alignment systems. Intramedullary alignment systems use the inside of the femur or tibia, the medullary canal, as one of the selected landmarks for establishing alignment. Extramedullary alignment systems use only the external surfaces of the body to establish alignment.

A typical extramedullary alignment system requires the surgeon to visually align a slender rod with the center of the knee and the center of the femoral head for alignment of the femoral component, then align a similar rod with the center of the ankle and the center of the tibial plateau for alignment of the tibial component. The centers of the femoral head and ankle are found by palpation or are established with an intraoperative X-ray. If correctly placed, the rods will lie parallel to, and offset from the mechanical axes. Once aligned, the rods are used as a guide to fix the location of the cutting guides with respect to the femur and the tibia so that the cuts can be performed.

A typical intramedullary alignment system requires the surgeon to insert rods into the medullary canal of the femur and of the tibia. If properly placed, these rods should lie on the respective axes of the bones. In the case of the tibia, the mechanical axis is very close to the axis of the bone. In the case of the femur, the axis of the bone is quite different from the mechanical axis due to the offset nature of the hip joint, and this difference must be measured from the pre-operative X-ray and used to correct the alignment of the femoral cutting guides.

Both intramedullary and extramedullary approaches to alignment have numerous inherent drawbacks and sources of error. Extramedullary alignment depends on accurate visual estimation of the alignment of the extramedullary rods. Location of the femoral head by palpation is difficult and error-prone, particularly with obese patients. Use of intraoperative X-rays improves the result somewhat, but is time consuming and exposes the patient and operating room personnel to radiation. X-rays also are subject to distortion and require visual interpretation and estimation to analyze correctly, as X-rays offer only one planar view in two dimensions.

Intramedullary alignment approaches provide only sightly better results, in that the knee joint alignment is still determined by estimating the difference between the bone axis and the mechanical axis from a potentially distorted X-ray image. In addition, intramedullary rods must be introduced very carefully, not only to make sure they align correctly with the medullary canal, but also to make sure that the insertion of the rods does not create an embolism, which could seriously injure or even kill the patient.

An ideal alignment system finds the mechanical axis of the patient's leg directly, without the need for preoperative or intraoperative X-rays, estimation, calculation, location of hidden or obscured landmarks, or surgical intervention outside of that required for access to the knee joint surfaces. The ideal alignment system depends only on the accepted definition that the mechanical axis passes through the center of the head of the femur, the center of the knee joint and the center of the ankle, in order to locate the mechanical axis.

In an earlier patent application in the U.S. Ser. No. 08/199,069, filed Feb. 22, 1994, now U.S. Pat. No. 5,601,566, the disclosure of which is incorporated herein by reference thereto, method and apparatus are disclosed for locating the mechanical axis of a patient's femur by directly locating the center of rotation of the head of the femur. An external alignment rod is affixed to the femur and extends in a direction parallel to the mechanical axis of the femur. The present invention provides apparatus and method by which the external alignment rod of the apparatus described in the above patent application, placed as described in that application, is employed to enable appropriate alignment of a tibial resection guide relative to the direction of the mechanical axis of the femur for a greater degree of accuracy in the placement of the components of the knee prosthesis with respect to the weight bearing axis, or mechanical axis, of the patient's leg. As such, the present invention attains several objects and advantages, some of which are summarized as follows: Enables the accurate location of the direction of the mechanical axis of the femur interoperatively, without invading the medullary canal and without the necessity for surgical intervention beyond that already required for access to the knee being replaced, to serve in the accurate location of the tibial component, as well as the femoral component of a knee prosthesis, during total knee replacement surgery; provides a relatively simple procedure capable of being performed quickly just prior to preparing the tibia for resection; attains a high degree of accuracy with minimal procedural steps and apparatus; enables a direct determination of the direction of the mechanical axis of the femur and the relative location of a tibial resection guide with less reliance upon visual estimation or interpretation; provides simplified apparatus capable of long-term reliable performance.

The above objects and advantages, as well as further objects and advantages, are attained by the present invention which may be described briefly as providing as an improvement in an apparatus for aligning a tibial resection guide relative to the direction of the mechanical axis of the leg of a recipient of a total knee prosthesis wherein the tibial resection guide is to be affixed to the tibia of the recipient, at the proximal tibia of the tibia, for resection of the proximal tibia, the tibia including a distal tibia, and wherein an external alignment rod is affixed to the femur and extends in the direction of the mechanical axis, an external tibial alignment shaft extends longitudinally along an alignment axis between an upper end and a lower end, the tibial alignment shaft having a proximal portion adjacent the upper end for placement adjacent the proximal tibia and a distal portion adjacent the lower end for placement adjacent the distal tibia, and proximal coupling means are placed adjacent the upper end of the tibial alignment shaft for selectively coupling the tibial resection guide to the proximal portion of the tibial alignment shaft, distal coupling means are located for selectively coupling the distal portion of tibial alignment shaft to the distal tibia, forward of the tibia, a proximal alignment member for placement on the proximal portion of the tibial alignment shaft, the proximal alignment member including an alignment guideway extending longitudinally along the proximal alignment member, parallel to the alignment axis of the tibial alignment shaft, the alignment guideway having an opening for reception of the external alignment rod into the alignment guideway, the alignment guideway being complementary to the external alignment rod such that upon reception of the external alignment rod into the alignment guideway, the proximal alignment member will be aligned with the external alignment rod to bring the proximal portion of the tibial alignment shaft into alignment with the direction of the external alignment rod for aligning the tibial resection guide relative to the direction of the mechanical axis of the leg.

The invention will be understood more fully, while still further objects and advantages will become apparent, in the following detailed description of preferred embodiments of the invention illustrated in the accompanying drawing, in which.

Figure 1:
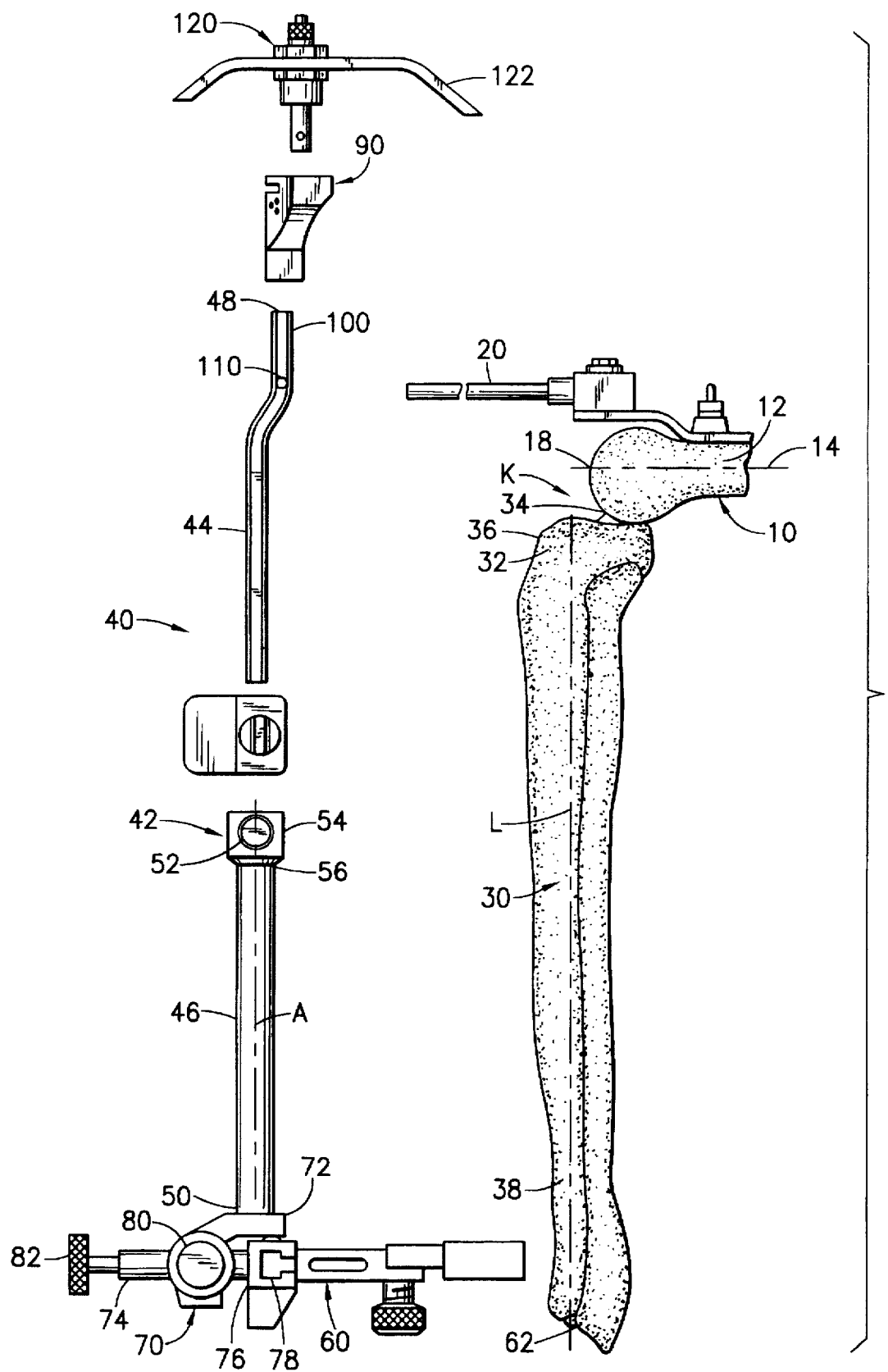
FIG. 1 is an exploded elevational view showing component parts of an apparatus constructed in accordance with the present invention and being placed into service for accomplishing the implant of a total knee prosthesis.

Referring now to the drawing, and especially to FIG. 1 thereof, a portion of the femur of a supine patient is illustrated somewhat schematically at 10 and is seen to include distal femur 12 at the knee K of the patient. As more fully described in the aforesaid patent application Ser. No. 08/199,069, the femur 10 is constrained for rotation about the femoral head (not shown) of the femur 10 and the mechanical axis 14 of the femur 10 passes through the center of rotation of the femoral head and the center 18 of the knee K of the patient. The direction of the mechanical axis 14 has been determined in the manner described in the aforesaid patent application and an elongate external alignment rod 20 has been affixed to the femur 10, extending in a direction parallel with the mechanical axis 14 of femur 10. Alignment rod 20, being parallel with the mechanical axis 14, is available for use in locating cutting guides for making the cuts necessary to prepare the distal femur 12 for the reception of a femoral knee prosthesis to be implanted, as described in the aforesaid patent application. The present invention enables the employment of alignment rod 20 for aligning a tibial resection guide as well, as will be described below.

Tibia 30 of the recipient includes proximal tibia 32, tibial eminence 34 and anterior cortex 36, and is to be prepared for the reception of the tibial component of a prosthetic knee implant (not shown) by resection of the proximal tibia 32. Tibia 30 includes a long axis L and distal tibia 38. Apparatus constructed in accordance with the invention for the preparation of the proximal tibia 32 is illustrated generally at 40 and is seen to include an external tibial alignment shaft 42 having a proximal, or upper portion in the form of an upper shaft portion 44 and a distal, or lower portion in the form of a tubular member 46. Tibial alignment shaft 42 extends longitudinally between an upper end 48 and a lower end 50 and upper shaft portion 44 is to be received within tubular member 46 in telescoping engagement adjacent the lower end 50, for selective movement relative to the tubular member 46 along a common alignment axis A. Clamping means, shown in the form of a thumbscrew 52 threaded through a collar 54 integral with the tubular member 46 at the upper end 56 of the tubular member 46, selectively clamps the upper shaft portion 44 in place at any location of upper shaft portion 44 along alignment axis A relative to tubular member 46, when the upper shaft portion 44 is telescoped into the tubular member 46.

Figure 2:
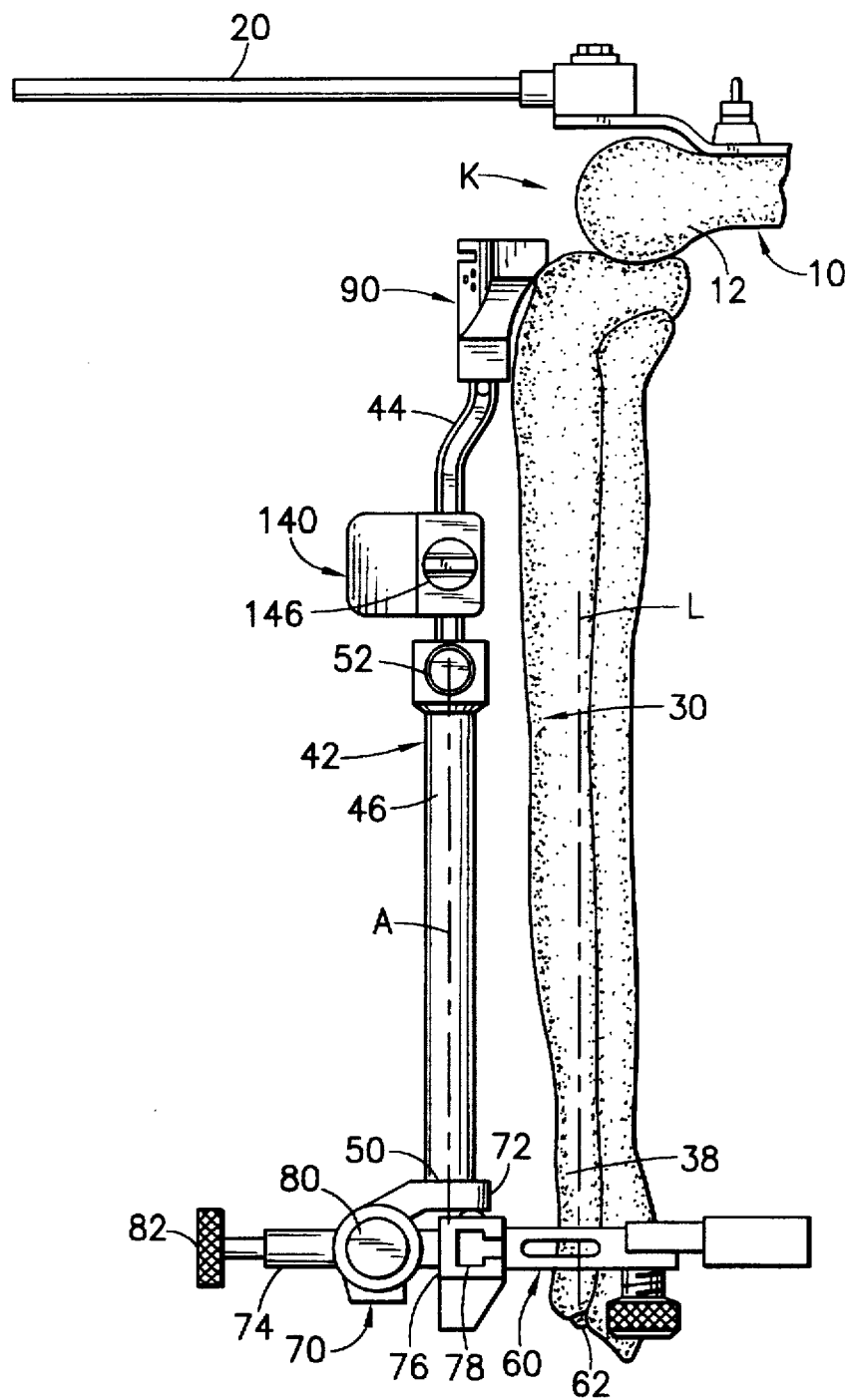
FIG. 2 is an elevational view showing the component parts assembled at the leg of a recipient of a total knee prosthesis, with the knee flexed.

Distal coupling means in the form of a lower clamp 60 is constructed as described in an earlier patent application in the U.S. Ser. No. 08/552,594, filed Nov. 3, 1995, the disclosure of which application is incorporated herein by reference thereto, and is mounted at the lower end of the tubular member 46, and, consequently, at the lower end 50 of the tibial alignment shaft 42. As seen in FIG. 2, lower clamp 60 is placed around the distal tibia 38, just above the malleoli, to be secured to the distal tibia 38, for selectively coupling and locating the lower end of the tubular member 46 and, consequently, the lower end 50 of the tibial alignment shaft 42, in alignment with the distal tibia 38, forward of the distal tibia 38, adjacent the ankle 62 of the recipient.

Alignment means is shown in the form of an alignment assembly 70 which includes a first carriage 72 integral with the lower end 50 of the tibial alignment shaft 42 and mounted for sliding movement along a first guideway 74 which, in turn, is carried by a second carriage 76 mounted for sliding movement along a second guideway 78 integral with clamp 60. The first guideway 74 has a rectangular cross-sectional configuration and extends in an anterior-posterior direction for enabling the first carriage 72 to be moved selectively along the first guideway 74 in anterior and posterior directions. The second guideway 78 has a T-shaped cross-sectional configuration and extends in a medial-lateral direction for enabling the second carriage 76 to be moved selectively along the second guideway 78 in medial and lateral directions. First and second carriages 72 and 76 are moved to align axis A of the tibial alignment shaft 42 with the center of ankle 62. Once the axis A is aligned as described, a first thumbscrew 80 in the first carriage 72 is tightened to secure the first carriage 72 in place on the first guideway 74, and a second thumbscrew 82 in the second carriage 76 is tightened to secure the second carriage 76 in place on the second guideway 78.

Figures 3, 4:
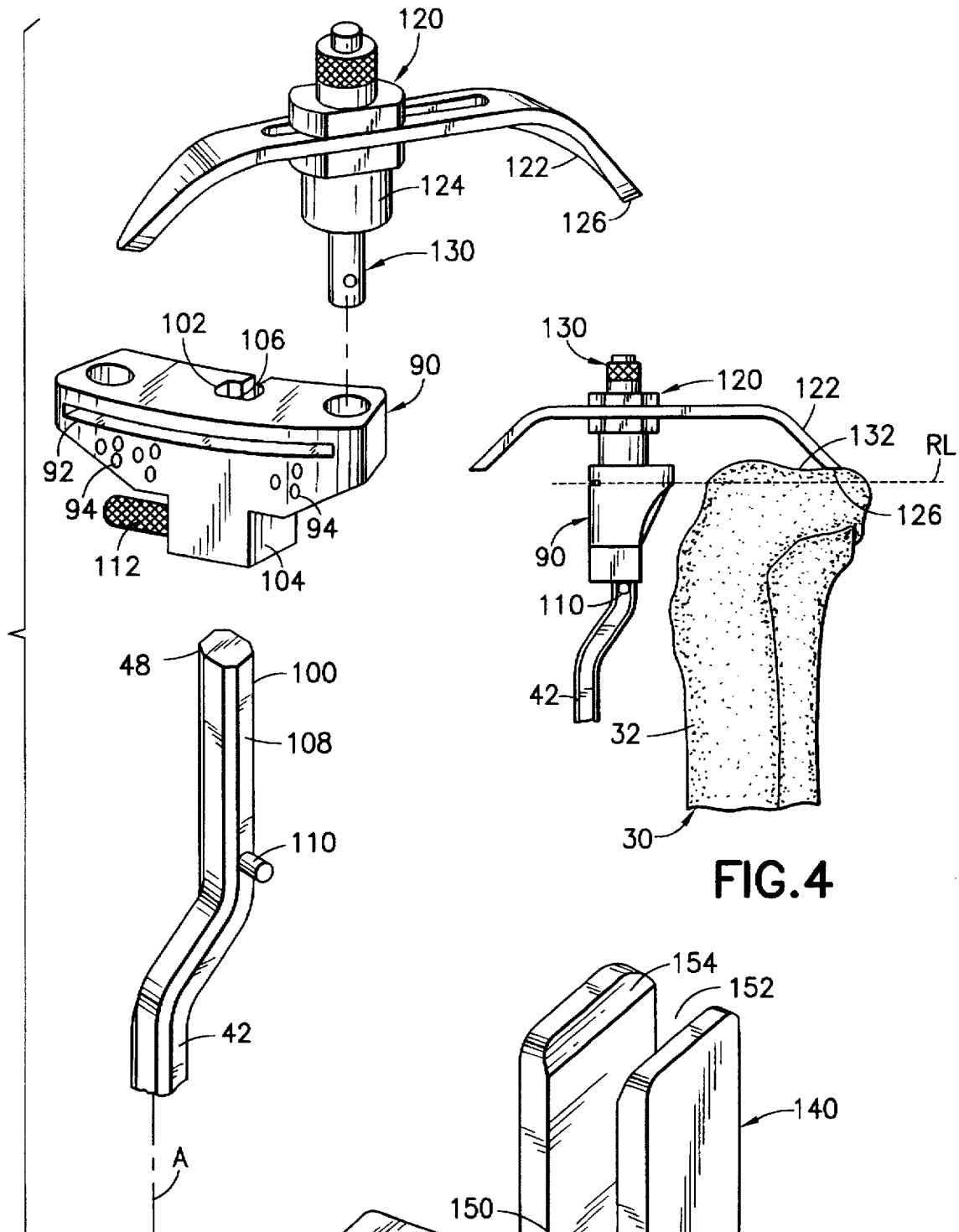
FIG. 3 is an enlarged exploded perspective view showing some of the component parts.
FIG. 4 is a fragmentary elevational view showing the component parts of FIG. 3 assembled in place.

Turning now to FIGS. 3 and 4, as well as to FIGS. 1 and 2, a tibial resection guide 90 is to be assembled with the tibial alignment shaft 42 and located at an appropriate resection location for the accomplishment of the desired proximal cut along the proximal tibia 32. To that end, tibial resection guide 90 includes a cutting guide surface, shown in the form of a saw blade guide slot 92 extending in a medial-lateral direction between the sides of the tibial resection guide 90 and through the tibial resection guide 90 in the anterior-posterior direction. A plurality of holes 94 also extend through the tibial resection guide 90 in the anterior-posterior direction, all as more fully described in the aforesaid patent application Ser. No. 08/552,594.

In order to assemble the tibial resection guide 90 with the tibial alignment shaft 42, proximal coupling means are provided and include an offset head 100 at the upper end 48 of the tibial alignment shaft 42 for the reception and selective securement of the tibial resection guide 90 to be selectively affixed to the tibial alignment shaft 42 by virtue of the engagement of the offset head 100 with a complementary channel 102 passing through the tibial resection guide 90, and an extension 104 thereof, in the direction parallel to the alignment axis A of the tibial alignment shaft 42 and having an inner surface 106 with a contour configuration generally complementary to the contour configuration of outer surface 108 of the offset head 100 of the tibial alignment shaft 42, at the upper end 48 of the tibial alignment shaft 42. The tibial resection guide 90 is seated against a stop pin 110, and then a thumbscrew 112, threaded in the tibial resection guide 90, is tightened to secure the tibial resection guide 90 in place.

The resection location of the tibial resection guide 90 is determined by a stylus assembly 120 which is most conveniently attached to the tibial resection guide 90 prior to placement of the tibial resection guide 90 on the tibial alignment shaft 42. Stylus assembly 120 includes a tibial stylus 122 mounted upon a stylus housing 124 and having a tip 126, and is selectively attached to and detached from the tibial resection guide 90 by attachment means shown in the form of a quick-connect mechanism 130, as more fully described in the aforesaid patent application Ser. No. 08/552,594.

Thus, as seen in FIGS. 2 and 4, upper shaft portion 44 of the tibial alignment shaft 42 is inserted into the tubular member 46 and is telescoped downwardly within tubular member 46, with the tibial resection guide 90 coupled to the upper shaft portion 44 of the tibial alignment shaft 42, until tibial stylus 122 of the stylus assembly 120 is seated upon proximal tibia 32, in contact with tibial eminence 34, with the tip 126 of tibial stylus 124 engaging the proximal tibia 32 along the tibial plateau 132, thereby placing the tibial resection guide 90 at the correct level for accomplishing the proximal cut at the desired resection level RL. The quick-connect mechanism 130 accomplishes a highly stable attachment of the stylus assembly 120 to the tibial resection guide 90 in a compact and easily operated arrangement. Once the tibial resection guide 90 is located at the desired resection level, the thumbscrew 52 is tightened, thereby securing the tibial resection guide 90 at the desired resection level RL, and the stylus assembly 120 is detached from the tibial resection guide 90 by merely operating the quick-disconnect mechanism 130.

Figure 5:
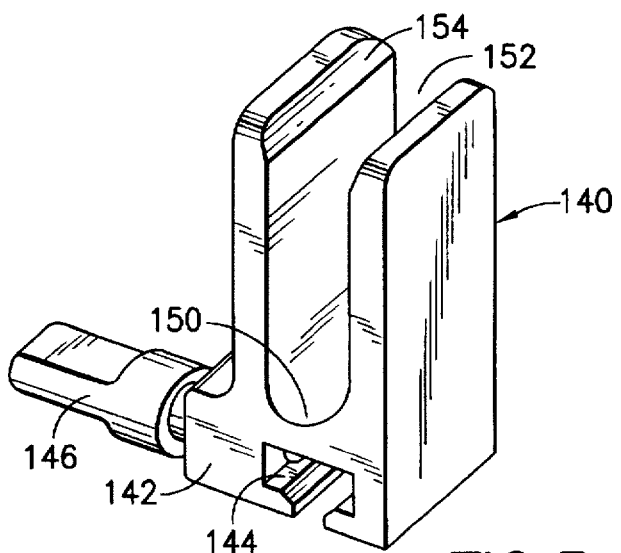
FIG. 5 is an enlarged perspective view of a component part constructed in accordance with the present invention.

In order to accomplish alignment of the tibial resection guide 90 appropriately relative to the direction of the mechanical axis 14 of the femur 10, a proximal alignment member 140 is placed upon the upper shaft portion 44 of the tibial alignment shaft 42, as illustrated in FIG. 2. Proximal alignment member 140 itself is best illustrated in FIG. 5 and is seen to include a block 142 and a channel 144 extending through the block 142, the channel 144 having a cross-sectional configuration complementary to the cross-sectional configuration of the upper shaft portion 44 of the tibial alignment shaft 42 for the reception of the upper shaft portion 44 within the channel 144. A thumbscrew 146 is threaded into the block 142 and communicates with the channel 144 to enable selective securement of the block 144 to the upper shaft portion 44 of the tibial alignment shaft 42, as seen in FIG. 2. An alignment guideway in the form of a slot 150 extends longitudinally along the block 142 of the proximal alignment member 140 and an opening 152 extends transversely to communicate with the slot 150 along the length of the slot 150 and includes a beveled entrance 154. The complementary cross-sectional configurations of the upper shaft portion 44 of the tibial alignment shaft 42 and the channel 144 of the proximal alignment member 140 assure that upon engagement of the upper shaft portion 44 within the channel 144, the slot 150 is aligned properly with the axis A of the tibial alignment shaft 42.

Figure 6:
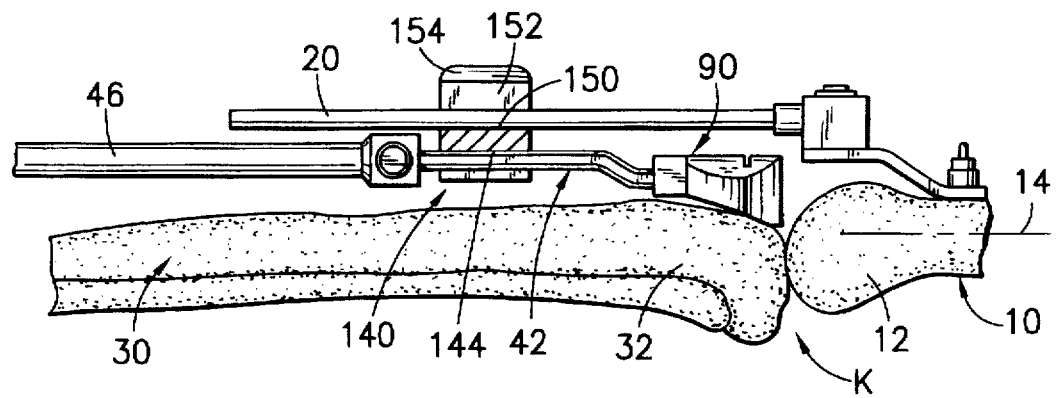
FIG. 6 is an elevational view similar to a fragment of FIG. 2, but with the knee of the recipient extended.
Figure 7:
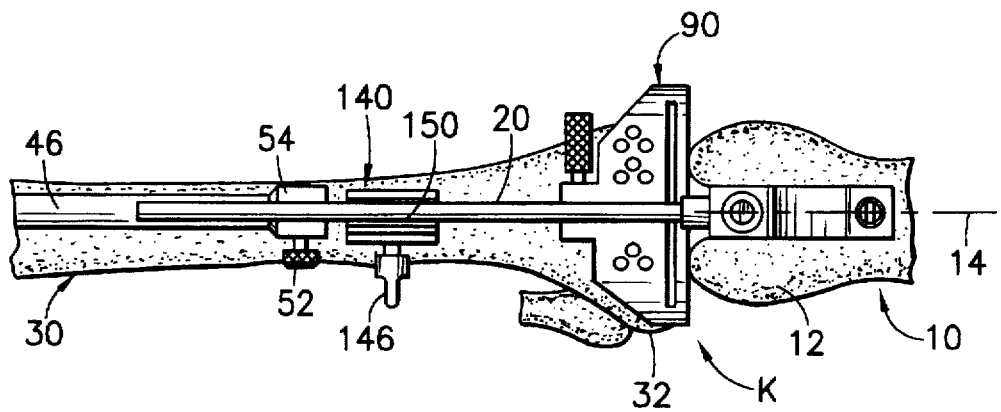
FIG. 7 is a plan view of the fragment shown in FIG. 6.

With the proximal alignment member 140 secured in place upon the upper shaft portion 44 of the tibial alignment shaft 42, the knee K is placed in extension, as shown in FIGS. 6 and 7. As the knee K is extended, the tibial alignment shaft 42 is manipulated so that the alignment rod 20 is engaged within the slot 150 of the proximal alignment member 140 to align the proximal alignment member 140 with the alignment rod 20 and, consequently, to align the tibial alignment shaft 42 with the direction of the alignment rod 20, thereby aligning the tibial resection guide 90 relative to the direction of the mechanical axis 14 of the femur 10 and, consequently, relative to the mechanical axis of the leg of the recipient. To this end, the tibial alignment shaft 42 is shifted, as required, during extension of the knee K, to receive the alignment rod 20 transversely through the beveled entrance 154 into the opening 152 and into the slot 150 of the proximal alignment member 140.

Figure 8:
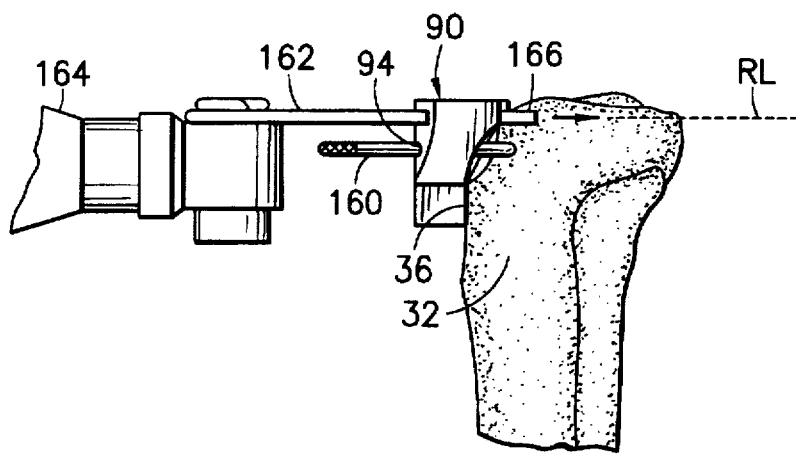
FIG. 8 is a fragmentary side elevational view showing resection of the tibia in accordance with the invention.

Turning to FIG. 8, once the tibial resection guide 90 is aligned relative to the direction of the mechanical axis 14, the tibial resection guide 90 is affixed to the proximal tibia 32, adjacent the anterior cortex 36, by affixation means, shown in the form of drill-pins 160 inserted through selected holes 94 in the tibial resection guide 90 and into the proximal tibia 32. Then, the alignment rod 20 is removed from the femur 10, the tibial alignment shaft 42 is uncoupled from the tibial resection guide 90, the knee K is flexed to ninety degrees, to bring the tibia 30 to the position illustrated in FIG. 8, and the tibial resection guide 90 is fully exposed for uninhibited access to the tibial resection guide 90 for resection of the proximal tibia 32. A saw blade 162 of a saw 164 then is inserted through the saw blade guide slot 92 to accomplish proximal cut 166 at the resection level RL.

It will be seen that the present invention attains the several objects and advantages summarized above, namely: Enables the accurate location of the direction of the mechanical axis of the femur interoperatively, without invading the medullary canal and without the necessity for surgical intervention beyond that already required for access to the knee being replaced, to serve in the accurate location of the tibial component, as well as the femoral component of a knee prosthesis, during total knee replacement surgery; provides a relatively simple procedure capable of being performed quickly just prior to preparing the tibia for resection; attains a high degree of accuracy with minimal procedural steps and apparatus; enables a direct determination of the direction of the mechanical axis of the femur and the relative location of a tibial resection guide with less reliance upon visual estimation or interpretation; provides simplified apparatus capable of long-term reliable performance.

It is to be understood that the above detailed description of preferred embodiments of the invention are provided by way of example only. Various details of design, construction and procedure may be modified without departing from the true spirit and scope of the invention, as set forth in the appended claims.

The embodiments of the invention in which an exclusive property or privilege is claimed are defined as follows:

1. Apparatus for aligning a tibial resection guide relative to the direction of the mechanical axis of the leg of a recipient of a total knee prosthesis wherein the tibial resection guide is to be affixed to the tibia of the recipient, at the proximal tibia of the tibia, for resection of the proximal tibia, the tibia including a distal tibia, and wherein an external alignment rod is affixed to the femur and extends in the direction of the mechanical axis, the apparatus comprising:

an external tibial alignment shaft extending longitudinally along an alignment axis between an upper end and a lower end, the tibial alignment shaft having a proximal portion adjacent the upper end for placement adjacent the proximal tibia and a distal portion adjacent the lower end for placement adjacent the distal tibia;

proximal coupling means adjacent the upper end of the tibial alignment shaft for selectively coupling the tibial resection guide to the proximal portion of the tibial alignment shaft;

distal coupling means for selectively coupling the distal portion of tibial alignment shaft to the distal tibia, forward of the tibia; and a proximal alignment member at the proximal portion of the tibial alignment shaft, the proximal alignment member including an alignment guideway extending longitudinally along the proximal alignment member, parallel to the alignment axis of the tibial alignment shaft, the alignment guideway having an opening for reception of the external alignment rod into the alignment guideway, the alignment guideway being complementary to the external alignment rod such that upon reception of the external alignment rod into the alignment guideway, the proximal alignment member will be aligned with the external alignment rod to bring the proximal portion of the tibial alignment shaft into alignment with the direction of the external alignment rod for aligning the tibial resection guide relative to the direction of the mechanical axis of the leg.

2. The invention of claim 1 wherein the alignment guideway includes a slot extending longitudinally along the proximal alignment member, and the opening extends in a transverse direction such that the proximal portion of the tibial alignment shaft is received in a transverse direction into the slot.

3. The invention of claim 1 wherein the proximal alignment member includes selective coupling means for selectively coupling and uncoupling the proximal alignment member and the proximal portion of the tibial alignment shaft.

4. The invention of claim 3 wherein the alignment guideway includes a slot extending longitudinally along the proximal alignment member, and the opening extends in a transverse direction such that the proximal portion of the tibial alignment shaft is received in a transverse direction into the slot.

5. The invention of claim 4 wherein the selective coupling means includes complementary cross-sectional configurations in the proximal alignment member and on the proximal portion of the tibial alignment shaft, the complementary cross-sectional configurations aligning the slot with the alignment axis of the tibial alignment shaft upon placement of the proximal alignment member on the proximal portion of the tibial alignment shaft.

6. In an apparatus for aligning a tibial resection guide relative to the direction of the mechanical axis of the leg of a recipient of a total knee prosthesis wherein the tibial resection guide is to be affixed to the tibia of the recipient, at the proximal tibia of the tibia, for resection of the proximal tibia, the tibia including a distal tibia, and wherein an external alignment rod is affixed to the femur and extends in the direction of the mechanical axis, an external tibial alignment shaft extends longitudinally along an alignment axis between an upper end and a lower end, the tibial alignment shaft having a proximal portion adjacent the upper end for placement adjacent the proximal tibia and a distal portion adjacent the lower end for placement adjacent the distal tibia, proximal coupling means are placed adjacent the upper end of the tibial alignment shaft for selectively coupling the tibial resection guide to the proximal portion of the tibial alignment shaft, and distal coupling means are located for selectively coupling the distal portion of tibial alignment shaft to the distal tibia, forward of the tibia, the improvement comprising:

a proximal alignment member for placement on the proximal portion of the tibial alignment shaft, the proximal alignment member including an alignment guideway extending longitudinally along the proximal alignment member, parallel to the alignment axis of the tibial alignment shaft, the alignment guideway having an opening for reception of the external alignment rod into the alignment guideway, the alignment guideway being complementary to the external alignment rod such that upon reception of the external alignment rod into the alignment guideway, the proximal alignment member will be aligned with the external alignment rod to bring the proximal portion of the tibial alignment shaft into alignment with the direction of the external alignment rod for aligning the tibial resection guide relative to the direction of the mechanical axis of the leg.

7. The invention of claim 6 wherein the alignment guideway includes a slot extending longitudinally along the proximal alignment member, and the opening extends in a transverse direction such that the proximal portion of the tibial alignment shaft is received in a transverse direction into the slot.

8. The invention of claim 6 wherein the proximal alignment member includes selective coupling means for selectively coupling and uncoupling the proximal alignment member and the proximal portion of the tibial alignment shaft.

9. The invention of claim 8 wherein the alignment guideway includes a slot extending longitudinally along the proximal alignment member, and the opening extends in a transverse direction such that the proximal portion of the tibial alignment shaft is received in a transverse direction into the slot.

10. The invention of claim 9 wherein the selective coupling means includes complementary cross-sectional configurations in the proximal alignment member and on the proximal portion of the tibial alignment shaft, the complementary cross-sectional configurations aligning the slot with the alignment axis of the tibial alignment shaft upon placement of the proximal alignment member on the proximal portion of the tibial alignment shaft.

11. Method for aligning a tibial resection guide relative to the direction of the mechanical axis of the leg of a recipient of a total knee prosthesis wherein the tibial resection guide is to be affixed to the tibia of the recipient, at the proximal tibia of the tibia, for resection of the proximal tibia, the tibia including a distal tibia, the method comprising:

affixing an external alignment rod to the femur such that the external alignment rod extends in the direction of the mechanical axis;

coupling a distal portion of an external tibial alignment shaft; and to the distal tibia, forward of the tibia, the external tibial alignment shaft extending longitudinally along an alignment axis and having a proximal portion adjacent the proximal tibia when the distal portion is coupled to the distal tibia;

coupling the tibial resection guide with the proximal portion of the tibial alignment shaft;

positioning the proximal portion of the tibial alignment shaft such that a proximal alignment member on the proximal portion of the tibial alignment shaft is engaged with the external alignment rod to align the proximal alignment member with the external alignment rod and bring the proximal portion of the tibial alignment shaft into alignment with the direction of the external alignment rod for aligning the tibial resection guide relative to the direction of the mechanical axis of the leg.

12. The invention of claim 11 wherein the proximal alignment member includes an alignment guideway extending longitudinally parallel to the alignment axis of the external tibial shaft, and the proximal alignment member is engaged with the external alignment rod by relative transverse movement between the proximal alignment member and the external alignment rod.

13. The invention of claim 11 including coupling the proximal alignment member with the proximal portion of the external tibial shaft prior to engagement of the proximal alignment member with the external alignment rod.

14. The invention of claim 13 wherein the proximal alignment member includes an alignment guideway extending longitudinally parallel to the alignment axis of the external tibial shaft, and the proximal alignment member is engaged with the external alignment rod by relative transverse movement between the proximal alignment member and the external alignment rod.

15. The invention of claim 14 including affixing the tibial resection guide to the proximal tibia subsequent to alignment of the tibial resection guide with the mechanical axis of the leg.

16. The invention of claim 15 including resecting the proximal tibia subsequent to affixing the tibial resection guide to the proximal tibia.

* * * * *